United States Patent [19]

Mason et al.

[11] Patent Number: 5,507,792
[45] Date of Patent: Apr. 16, 1996

[54] THERAPEUTIC TREATMENT DEVICE HAVING A HEAT TRANSFER ELEMENT AND A PUMP FOR CIRCULATING A TREATMENT FLUID THERETHROUGH

[75] Inventors: Bradley R. Mason, Olivenhain; Jeffrey T. Mason, Escondido, both of Calif.

[73] Assignee: Breg, Inc., Vista, Calif.

[21] Appl. No.: 273,020

[22] Filed: Jul. 8, 1994

Related U.S. Application Data

[63] Continuation-in-part of Ser. No. 850,071, Mar. 12, 1992, Pat. No. Des. 352,781, Ser. No. 100,047, Jul. 30, 1993, Pat. No. 5,330,519, and Ser. No. 199,333, Feb. 22, 1994, which is a continuation-in-part of Ser. No. 100,047, Jul. 30, 1993, Pat. No. 5,330,519, Ser. No. 172,022, Dec. 21, 1993, and Ser. No. 69,195, May 27, 1993, said Ser. No. 100,047, is a continuation of Ser. No. 767,494, Sep. 30, 1991, Pat. No. 5,241,951, which is a continuation-in-part of Ser. No. 578,508, Sep. 5, 1990, Pat. No. 5,080,089, said Ser. No. 172,022, is a continuation-in-part of Ser. No. 69,195, which is a continuation-in-part of Ser. No. 906,407, Jul. 1, 1992, Pat. No. 5,324,319, and Ser. No. 851,345, Mar. 12, 1992, Pat. No. Des. 345,609, said Ser. No. 906,407, is a continuation-in-part of Ser. No. 767,494, said Ser. No. 851,345, is a continuation-in-part of Ser. No. 767,494.

[51] Int. Cl.[6] ............................................. A61H 9/00
[52] U.S. Cl. .............................. 607/104; 607/108; 601/15
[58] Field of Search ........................... 607/104, 108, 607/109, 110, 111, 112; 602/14, 13; 601/15; 128/DIG. 20

[56] References Cited

U.S. PATENT DOCUMENTS

| | | | |
|---|---|---|---|
| 787,920 | 4/1905 | Hofmann | 607/104 |
| 3,894,213 | 7/1975 | Agarwala | 607/104 |
| 4,184,537 | 1/1980 | Sauder | 607/104 |
| 4,459,468 | 7/1984 | Bailey | 607/104 |
| 4,702,235 | 10/1987 | Hong | 602/13 |
| 4,951,665 | 8/1990 | Schneider | 607/104 |
| 5,372,608 | 12/1994 | Johnson | 607/104 |

OTHER PUBLICATIONS

"Aircast AutoChill System", Aircast Incorporated, Oct. 1993.
"Aircast Cryo/Cuff", Aircast Incorporated, 1991.

*Primary Examiner*—Richard J. Apley
*Assistant Examiner*—Jeanne M. Clark
*Attorney, Agent, or Firm*—Rodney F. Brown

[57] ABSTRACT

A device is provided for therapeutically treating a desired region of a patient's body with a nonambient temperature treatment fluid circulated through a pliant heat transfer element positioned on the treatment region. In accordance with one embodiment, the device has a fluid inlet line supplying the treatment fluid to the heat transfer element from a fluid reservoir, and a fluid outlet line returning the treatment fluid to the fluid reservoir from the heat transfer element. The inlet and outlet lines are enclosed within a unitary sheath and a manual bulb pump is provided for driving the nonambient temperature treatment fluid between the reservoir and the heat transfer element. In accordance with another embodiment, fluid drive is provided by a motor-driven submersible pump positioned in the reservoir. Temperature control of the heat transfer element is enabled by adjusting the fluid flow rate therethrough. In accordance with yet another embodiment, the device has a pump and a single fluid flow line. A network of valves and fittings are provided in the fluid flow line to enable alternate fluid flow from the reservoir to the heat transfer element and from the heat transfer element to the reservoir.

12 Claims, 7 Drawing Sheets

THERAPEUTIC TREATMENT DEVICE HAVING A HEAT TRANSFER ELEMENT AND A PUMP FOR CIRCULATING A TREATMENT FLUID THERETHROUGH

This patent application is a continuation-in-part patent application of the following co-pending patent applications:

| Serial Number | Filing Date |
| --- | --- |
| 07/850,071 | March 12, 1992 |
| 08/100,047 | July 30, 1993 |
| 08/199,333 | February 22, 1994 |

Ser. No. 08/199,333 filed Feb. 22, 1994 is a continuation-in-part of Ser. Nos. 08/100,047 filed Jul. 30, 1993; 08/172,022 filed Dec. 21, 1993 and 08/069,195 filed May 27, 1993. Ser. No. 08/100,047 issued as U.S. Pat. No. 5,330,519 is a continuation of Ser. No. 07/767,494 filed Sep. 30, 1991 issued as U.S. Pat. No. 5,241,951, which is a continuation-in-part of Ser. No. 07/578,508 filed Sep. 5, 1990 issued as U.S. Pat. No. 5,080,089. Ser. No. 08/172,022 filed Dec. 21, 1992 is a continuation-in-part of Ser. No. 08/069,195, filed May 27, 1993, which is a continuation-in-part of Ser. No. 07/906,407 filed Jul. 1, 1992 issued as U.S. Pat. No. 5,324,319, and of Ser. No. 07/851,345 filed Mar. 12, 1992 issued as U.S. Pat. No. Des. 345,609. Ser. Nos. 07/906,407 filed Jul. 1, 1992 and 07/851,345, filed Mar. 12, 1992, are both continuation-in-parts of Ser. No. 07/767,494 filed Sep. 30, 1991.

TECHNICAL FIELD

The present invention relates generally to therapeutic treatment of the body. The present invention particularly relates to an apparatus for treating bodily injuries or ailments by cooling or heating the affected region of the body. The present invention-more particularly, though not exclusively, relates to an apparatus for applying a heat transfer element having a nonambient temperature fluid circulated therethrough, to the external skin surface of the affected region.

BACKGROUND OF THE INVENTION

Bodily injuries and ailments, particularly those related to sports and leisure activities, are often treated by topically applying a heat transfer element containing a nonambient temperature material to the external skin surface of the affected region of the body. For example, a heat transfer element that contains a low temperature material in the form of ice or a cold liquid is commonly applied to the external skin surface of an injured or ailing body region, advantageously inhibiting swelling thereof. Alternatively, a heat transfer element that contains a high temperature material in the form of hot water or an active heating element is applied to the external skin surface of an injured or ailing body region, advantageously reducing pain or promoting healing thereof.

A number of splint devices incorporating a heat transfer element are known in the art for topically applying nonambient temperature materials to the external skin surface of an injured or ailing body region as evidenced by U.S. Pat. No. 3,548,819 to Davis et al; U.S. Pat. No. 3,901,225 to Sconce; and U.S. Pat. No. 4,706,658 to Cronin. One disadvantage of such devices is that the low temperature materials become too warm during treatment because the body continuously transfers heat to the low temperature materials as they remain in contact with the external skin surface. Conversely, high temperature materials become too cool during treatment because the high temperature materials continuously transfer heat to the body. This disadvantage can be remedied by periodically replacing the nonambient temperature materials in the heat transfer element of the device. Although periodic replacement of the nonambient temperature materials avoids substantial treatment temperature fluctuations, it is cumbersome and inconvenient such that replacement of the materials is often neglected to the detriment of the treatment.

In response to this problem, a number of alternate treatment systems have been developed, wherein a cooling or heating fluid is continuously circulated by a motor-driven pump from a low or high temperature fluid reservoir to the heat transfer element. Such systems are typified by U.S. Pat. No. 2,726,658 to Chessey; U.S. Pat. No. 3,683,902 to Artemenko et al; and U.S. Pat. No. 4,962,761 to Golden. These systems are noteworthy in that they are relatively complex and thus, costly to manufacture and maintain, as well as being somewhat difficult to operate. Accordingly, the systems are not particularly practical for general use.

In contrast, a treatment device is disclosed by U.S. Pat. No. 787,920 to Hofmann having a manual pump, rather than a motor-driven pump, for periodically circulating a cooling or heating fluid from a fluid reservoir to the heat transfer element. The heat transfer element is a rigid hollow probe having a fixed elongate tubular configuration for application to the concave surface of a body cavity, such as the rectum. Because the heat transfer element of the Hofmann device lacks flexibility or a planar surface, it is not adaptable to topical application on external skin surfaces, particularly where the surface is relatively planar or convex. Accordingly, the device of Hofmann has little utility for topical treatment of injured or ailing body regions on or proximally underlying the external skin surface.

Given the proliferation of sports and leisure activities and the proliferation of injuries associated therewith, a widespread need exists for a practical therapeutic nonambient temperature treatment device applicable to the external skin surfaces of the body. Therefore, it is an object of the present invention to provide a device that maintains a relatively stable treatment temperature at a desired external skin surface by applying a heat transfer element containing a nonambient temperature treatment fluid to the external skin surface. It is another object of the present invention to provide such a device wherein the heat transfer element is conformable to the contours of the external skin surface. It is still another object of the present invention to provide such a device having a mechanism for circulating the nonambient temperature treatment fluid through the heat transfer element. It is a further object of the present invention to provide such a device that is relatively simple to operate and inexpensive to produce and maintain. It is yet another object of the present invention to provide such a device that can be employed in the home or in the workplace enabling cost-effective treatment that does not significantly disrupt the daily schedule of the user.

SUMMARY OF THE INVENTION

The present invention is a device for therapeutically treating a desired region of the body by raising or lowering the temperature of the treatment region. The therapeutic treatment device comprises a heat transfer element, a fluid reservoir, a fluid flow line providing fluid communication between the heat transfer element and the fluid reservoir, and a pump providing a means for driving a nonambient temperature treatment fluid between the heat transfer element and the reservoir via the fluid flow line. The device is designed to be portable insofar as it is readily transportable for set up and use at varied locations.

The heat transfer element is a fluid-retaining bladder that has a pliant heat transfer surface enabling heat exchange between the treatment fluid retained within the bladder and the desired treatment region of the body upon which the bladder is positioned. The bladder is preferably a pad having a planar, yet pliant, construction that is capable of conforming to convex, concave or planar contours of the external skin surface on or proximally overlying the desired treatment region. The pad is provided with a pad inlet port, a pad outlet port, and a continuous tortuous pad flowpath extending through the pad from the pad inlet port to the pad outlet port. The nonambient temperature treatment fluid is either a cooling or heating fluid, that is circulated through the pad flowpath.

The fluid reservoir is a passive vessel providing a source for the nonambient temperature treatment fluid. The passive vessel is well-insulated to impede heat transfer between the treatment fluid and the external environment across the vessel walls, thereby requiring no active heating or cooling element to maintain the nonambient temperature of the treatment fluid. The passive vessel preferably has a substantially larger volume than the volume of the heat transfer element to contain an ample supply of fresh nonambient temperature treatment fluid. The pump is either manual or motor-driven and provides a sufficient drive force to transfer treatment fluid between the heat transfer element and the fluid reservoir via the fluid flow line, displace spent treatment fluid from the heat transfer element, and pressurize fresh treatment fluid in the heat transfer element.

In accordance with one embodiment of the present invention, the therapeutic treatment device has a pair of fluid flow lines providing two fluid pathways between the heat transfer element and the fluid reservoir in fluid isolation from one another. One fluid flow line is an inlet line supplying fresh nonambient temperature treatment fluid to the heat transfer element from the fluid reservoir and the other fluid flow line is an outlet line returning spent treatment fluid to the fluid reservoir from the heat transfer element. The fluid flow lines are integrally maintained within a unitary tubular sheath to facilitate operation of the therapeutic treatment device without kinking, tangling or otherwise disrupting the fluid flow lines.

A preferred sheath comprises a unitary structure having two longitudinal bores therethrough forming the inlet and outlet lines, an axial wall of heat-insulative material positioned between the inlet line and the outlet line to minimize heat exchange between the two flow lines, and a radial wall of heat-insulative material positioned between the external environment and each of the flow lines to minimize heat exchange between the external environment and the flow lines. A liner tube also concentrically extends through each bore to prevent treatment fluid leakage through or around the sheath. An alternate preferred sheath substitutes a heat transfer material for the heat-insulative material of the axial wall to facilitate, rather than minimize, heat exchange between the inlet line and the outlet line.

In accordance with another embodiment of the present invention, the therapeutic treatment device has only one fluid flow line providing a single fluid pathway between the heat transfer element and the fluid reservoir to alternately supply fresh nonambient temperature fluid to the heat transfer element from the fluid reservoir and return spent treatment fluid to the fluid reservoir from the heat transfer element. Various configurations of fittings associated with the fluid flow line and pump are provided enabling selective supply or return of the treatment fluid between the heat transfer element and fluid reservoir. The fittings include a straight coupling joining an end of the fluid flow line to the port of the heat transfer element where the heat transfer element has only a single alternate inlet and outlet port. The fittings also include a pair of leak-back valves positioned at the inlet and outlet ports of the pump. The leak-back valves permit substantially unrestricted flow at a full flow rate in the direction of the heat transfer element and permit restricted leak-back flow in the direction of the fluid reservoir at a substantially reduced flow rate.

Where the heat transfer element has two separate inlet and outlet ports in the manner of the pad described above, a "Y" coupling is provided to join the heat transfer element with the fluid flow line. In addition to the pump leak-back valves, a one-way valve positioned at the inlet port of the heat transfer element is provided permitting flow only in the direction of the heat transfer element and a flow restriction positioned at the outlet port of the heat transfer element is provided permitting restricted flow in either direction.

The pump of the above-recited embodiment is preferably a manually compressible bulb positioned in the flow line. Other manual or motor-driven pumps, however, can be substituted for the compressible bulb. For example, a reversible rotary impeller pump can be provided to selectively operate in either of two directions, driving fluid through the fluid flow line in the direction of the heat transfer element or, alternatively, driving fluid through the fluid flow line in the direction of the fluid reservoir as selected by the operator, thereby eliminating the leak-back valves from the inlet and outlet of the pump.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figures 1, 2A:
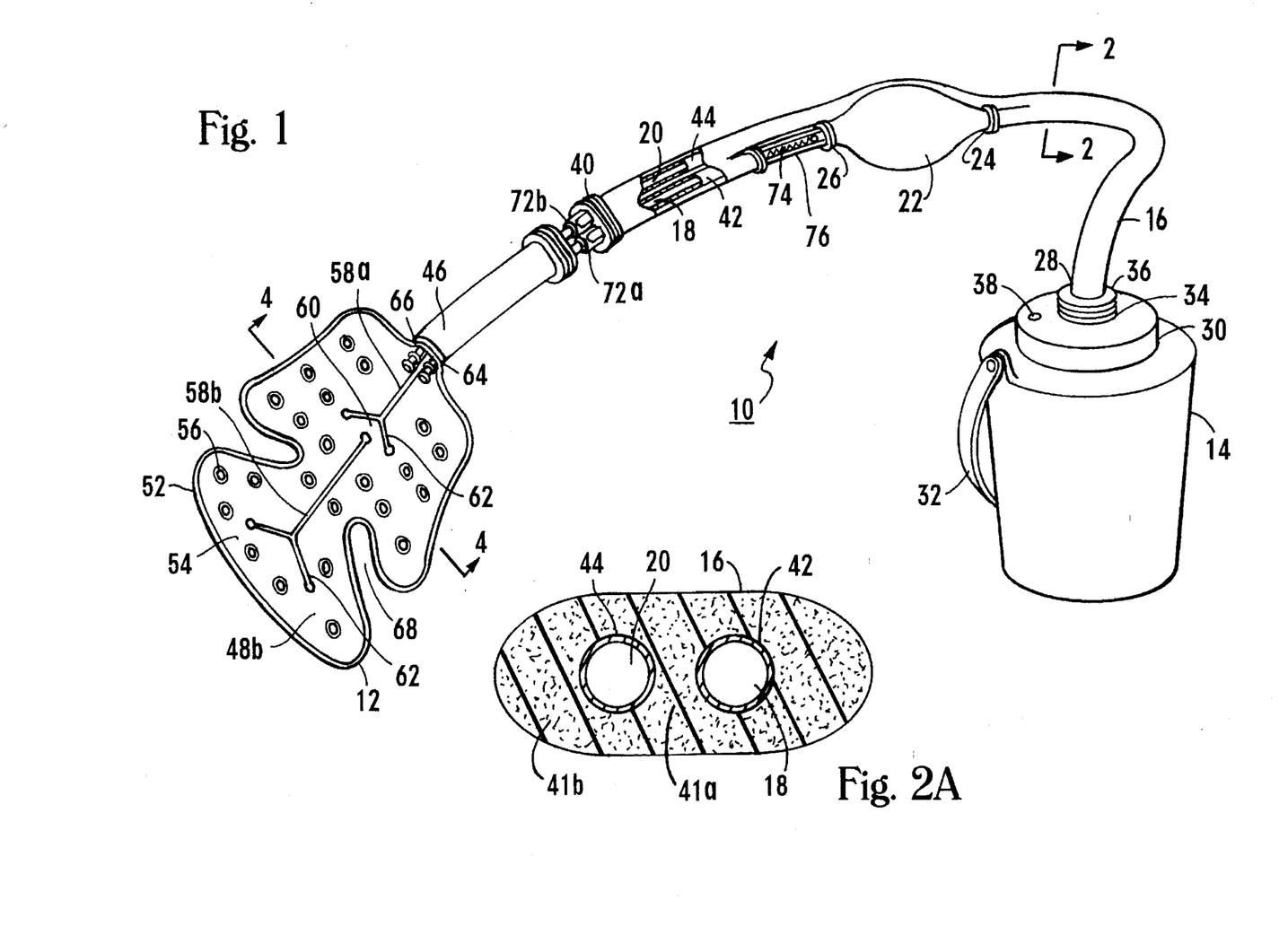
FIG. 1 is a perspective view of an embodiment of a therapeutic treatment device of the present invention having a fluid inlet line, a fluid outlet line, and a manual bulb pump positioned across the inlet line.
FIG. 2A is a cross-sectional elevational view of the sheath of FIG. 1 taken along line 2—2.

Referring initially to FIG. 1, the therapeutic treatment device of the present invention is shown and generally designated as 10. The present therapeutic treatment device 10 has a high temperature embodiment and a low temperature embodiment which are substantially identical in structure, differing only in the nonambient temperature of a treatment fluid circulated therethrough. Accordingly, the description of the therapeutic treatment device 10 as shown and set forth below applies generally to both the high and low temperature embodiments.

The therapeutic treatment device 10 comprises a pliant fluid-retaining heat transfer element in the form of a hollow pad 12, a fluid reservoir 14, and a unitary tubular sheath 16 enclosing a pair of fluid lines extending between the pad 12 and the fluid reservoir 14. A portion of the sheath 16 is cut away in FIG. 1 for purposes of illustration exposing the fluid lines 18, 20 enclosed by the sheath 16. The therapeutic treatment device 10 further comprises a pump 22 for driving a treatment fluid between the pad 12 and the fluid reservoir 14 via the fluid lines 18, 20. The pump 22 is a compressible, elastomeric bulb having good memory characteristics enabling the bulb pump 22 to be elastically deformed by compression, yet return to its original shape following compression as will be described hereafter. The bulb pump 22 is positioned in-line across the inlet line 18 at an intermediate point in the line 18 relatively distal to both the pad 12 and the fluid reservoir 14. The bulb pump 22 is provided with a pump inlet port 24 and a pump outlet port 26 enabling fluid communication between the interior chamber of the bulb pump 22, the pad 12 and the fluid reservoir 14 via the inlet line 18.

The fluid reservoir 14 is remotely positioned relative to the pad 12 and bulb pump 22 at the reservoir end 28 of the tubular sheath 16 and the associated fluid inlet and outlet lines 18, 20. Fluid reservoirs having present utility can be substantially any fluid container, although the preferred fluid reservoir 14, as shown herein, is a well-insulated passive vessel with impeded heat transfer between the fluid and the external environment across the vessel walls. As a passive vessel, the fluid reservoir 14 requires no active heating or cooling element to maintain the nonambient temperature of the treatment fluid therein.

In particular, the fluid reservoir 14 shown herein is a conventional heat-insulative water jug having a removable lid 30 and a handle 32 for ease of carrying. The lid 30 is removed from the reservoir 14 when it is desired to replace the treatment fluid, but the lid 30 is retained in place on the reservoir 14 during operation of the therapeutic treatment device 10 to maintain the nonambient temperature of the treatment fluid. An opening 34 is formed through the lid 30, enabling the reservoir end 28 of the fluid lines 18, 20 to fluid communicate with the reservoir 14 across a fitting 36 when the lid 30 is in place. A relatively small vent opening 38 is also formed through the lid 30 to vent the interior of the reservoir 14 to the atmosphere.

The reservoir 14 retains an excess of the nonambient temperature treatment fluid exceeding the capacity of the pad 12 and fluid lines 18, 20. In the low temperature embodiment of the present invention, the treatment fluid is a fluid cooled below ambient room temperature, such as ice water. In the high temperature embodiment of the invention, the treatment fluid is a fluid heated above ambient room temperature, such as hot water.

Referring to FIG. 2A in conjunction with FIG. 1, the unitary tubular sheath 16 is shown to be an extended length of tubular material having a first longitudinal bore formed therethrough which is the fluid inlet line 18 providing fluid communication between the pad 12 and the reservoir 14 in the direction of the pad 12. The sheath 16 further has a second longitudinal bore formed therethrough which is the fluid outlet line 20 providing fluid communication between the pad 12 and the reservoir 14 in the direction of the reservoir 14. The sheath 16 is substantially continuous along the length of the fluid flowpath between the pad 12 and the fluid reservoir 14, being interrupted only by in-line components of the device 10, such as the bulb pump 22 and a selectively releasable joint 40 positioned across the inlet and outlet lines 18, 20 in a manner described hereafter. The sheath 16 integrates the inlet and outlet lines 18, 20 into a single unitary structure that defeats kinking, tangling or other similar disruptions of the lines 18, 20, thereby facilitating uninterrupted operation of the therapeutic treatment device 10.

The tubular sheath 16 is formed from an elastic, resilient, heat-insulative foam that resists such kinking or tangling of the flow lines 18, 20. The sheath 16 has an axial heat-insulative wall 41a having relatively low heat transfer properties positioned between the inlet line 18 and the outlet line 20 impeding heat exchange between the lines 18, 20. The sheath further has a radial heat-insulative wall 41b positioned between the external environment and each of the flow lines 18, 20 impeding heat exchange therebetween. The inlet line 18 has an inlet liner tube 42 fitted therein and extending coaxially therethrough. The inlet liner tube 42 is formed from a solid (i.e., non-foam), high-strength, flexible, substantially fluid-impermeable material, such as polyurethane, having an outside diameter about equal to the inside diameter of the inlet line 18. The outside diameter of the inlet liner tube 42 is typically about 5/16 inches and the inside diameter of the inlet liner tube 42 is typically about 3/16 inches. The outlet line 20 likewise has an outlet liner tube 44 fitted therein that is substantially identical to the inlet liner tube 30.

The liner tubes 42, 44 prevent leakage of treatment fluid from the inlet line 18 or outlet line 20 into the sheath 16 or the external environment when treatment fluid is present in the lines 18, 20. The liner tubes 42, 44 also facilitate leak-proof connection and fluid communication between the inlet and outlet lines 18, 20 and the in-line components of the therapeutic treatment device 10, including the pad 12, the fluid reservoir 14, the bulb pump 22 and the releasable joint 40. The sheath 16 further functions to prevent condensate formation on the exterior of the liner tubes 42, 44 when the nonambient temperature treatment fluid is contained therein.

Figures 2B, 3, 4:
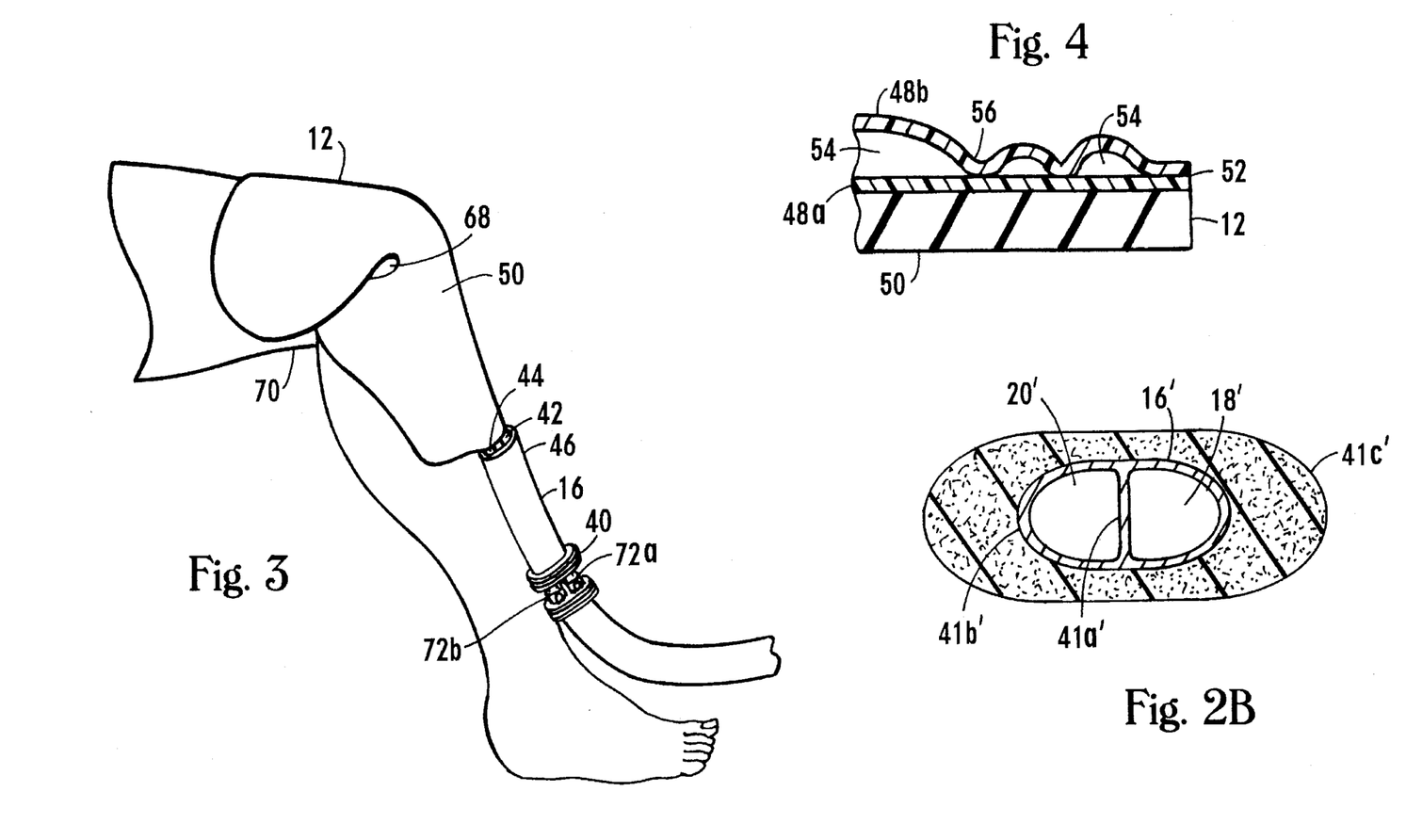
FIG. 2B is a cross-sectional elevational view of an alternate sheath.
FIG. 3 is a perspective view of the pad of FIG. 1 conformably positioned on the knee of a user.
FIG. 4 is a cross-sectional elevational view of the pad of FIG. 1 taken along line 4—4.

Referring to FIG. 2B, an alternate unitary tubular sheath 16' is shown comprising an axial wall 41a' and a radial wall 41b'. The sheath 16' is similar to the sheath 16 of FIG. 2A except that the sheath 16' is formed from a material having substantially the same properties as the liner tubes 42, 44 described above. Accordingly, liner tubes are not utilized in the sheath 16'. The material of the sheath 16' is preferably a heat-conductive material having high heat transfer properties relative to the material of the sheath 16. In any case, the axial wall 41a' of the sheath 16' is relatively thin, thereby facilitating heat exchange between the treatment fluid in the inlet line 18' and the treatment fluid in the outlet line 20' enclosed by the sheath 16'. Heat exchange between the inlet and outlet lines 18', 20' reduces the temperature difference between the fresh treatment fluid entering the pad 12 and the spent treatment fluid exiting the pad 12 to lessen the trauma to the user caused by extreme temperature differences within the pad 12. The sheath 16' is enclosed within a jacket 41c' of heat-insulative material having substantially the same properties as the sheath 16 described above to impede heat exchange between the external environment and each of the flow lines 18', 20' and further to prevent condensate formation on the exterior of the sheath 16'.

Referring again to FIG. 1, the pad 12 is shown to be remotely positioned relative to the fluid reservoir 14 at the pad end 46 of the sheath 16 and associated fluid inlet and outlet lines 18, 20 opposite the reservoir end 28 thereof. The pad 12 serves as the heat transfer element having a planar, pliant or flexible construction that is readily conformable to the contours of the external skin surface of the user. The planar pad 12 is characterized as having three dimensions, but wherein the thickness of the pad 12 is very small relative to the length and width of the pad 12. The planar pad 12 is additionally characterized as capable of being spread out flat in a resting position as shown in FIG. 1, but, due to the pliancy of the pad 12, also capable of being conformed to the three-dimensional contours of the external skin surface in an operating position as shown in FIG. 3. Pads, having substantially the same construction and configuration as the pad 12 of FIG. 1, are disclosed in U.S. patent application Ser. Nos. 08/069,195 and 08/172,022, both of which are incorporated herein by reference.

Referring to FIGS. 1 and 4, the pad 12 is shown to have a laminar construction, including an upper sheet 48a overlying a lower sheet 48b. Both sheets 48a, 48b are formed from a thin flexible heat-conductive material, such as transparent polyurethane. The outer face of the lower sheet 48b is exposed to engage the external skin surface when the pad 12 is operatively positioned on the body of a user. The outer face of the upper sheet 48a is bonded to a relatively thicker heat-insulative sheet 50 of a flexible foam material to prevent either heat loss through the upper sheet 48a to the surrounding environment, or heat gain through the upper sheet 48a from the surrounding environment. The heat-insulative sheet 50 also reduces fluid condensation on the outside of the pad 12. The peripheries of sheets 48a, 48b are bonded together by thermal welding to form a substantially planar bladder bounded by a peripheral seam 52. The interior of the bladder constitutes a pad flowpath 54. Further construction details with respect to specific materials having utility in the present invention, as well as to specific methods for bonding the materials together as required by the present invention, are well known in the art, for example, as disclosed in U.S. Pat. No. 5,086,771, incorporated herein by reference.

In addition to the peripheral seam 52, a plurality of circular welds 56 bond the sheets 48a, 48b together at periodic points across the pad 12. The circular welds 56 function to divert fluid flow in a tortuous manner through the pad flowpath 54. The circular welds 56 also function to limit the height and correspondingly the volume of the pad flowpath 54 when operating under elevated pressure. A plurality of linear welds also bond the sheets 48a, 48b together across the pad to delineate the pad flowpath 54. First and second linear welds 58a, 58b are aligned end to end along the longitudinal axis of the pad 12, separated at their ends by a narrow breach 60. The breach 60 enables a limited degree of cross flow within the pad flowpath 54, thereby improving temperature distribution across the pad 12 during operation, and enabling continued operation should kinks occur in the pad 12. Additional delineation of the pad flowpath 54 is provided by orthogonally or diagonally oriented linear welds 62 extending from the ends of the first and second linear welds 58a, 58b.

The pad 12 is further provided with a pad inlet port 64 through the seam 52 slightly offset to one side of the first linear flow divider 58a. A pad outlet port 66 is similarly provided in the seam 52 substantially adjacent to the pad inlet port 64, but slightly offset to the opposite side of the first linear flow divider 58a. The inlet and outlet liner tubes 42, 44 at the pad end 46 of the fluid lines 18, 20 penetrate the pad flowpath 54 through the pad inlet and outlet ports 64, 66, respectively, to provide fluid communication between the pad flowpath 20 and the exterior of the pad 12. The inlet and outlet liner tubes 42, 44 are sealingly bonded to the sheets 48a, 48b proximal to the pad inlet and outlet ports 64, 66, respectively, to prevent fluid leakage from the inlet and outlet lines 18, 20.

A plurality of cut-outs 68 are formed in the periphery of the pad 12 to facilitate conformance of the pad 12 to the external skin surface of the body. Referring to FIG. 3, the pad 12 is shown conformed to the convex external skin surface of the knee joint 70. The pad 12 overlies the knee joint 70 with the lower sheet 48b contacting the external skin surface of the joint 70 and with the heat-insulative sheet 50 exposed to the environment. The cut-outs 68 enable the user to arrange the planar pad 12 in a configuration that substantially close-fittingly encloses the convex knee joint 70 without substantially kinking the pad flowpath 54.

It is apparent that the pad 12 can alternatively be conformed to other external skin surfaces of the body in a like manner, and in particular to other substantially convex contoured external skin surfaces such as the shoulder, elbow, and hip. It is further apparent that although the therapeutic treatment device 10 is shown and described with reference to a single pad configuration, the present invention is not limited to any one specific pad configuration. Other planar pliant pads fall within the scope of the present invention, such as disclosed in U.S. Pat. Nos. Des. 345,609; and Des. 348,106; and in U.S. patent application Ser. Nos. 29/002, 338; and 29/002,333, all incorporated herein by reference.

The releasable joint 40 is provided in the fluid lines 18, 20 between the pad 12 and bulb pump 22 relatively proximal to the pad 12 to enable selective dissociation of the pad 12 from the therapeutic treatment device 10 during periods of inoperation, thereby facilitating interchangeability or removal of the pad 12 for storage or cleaning. The joint 40 shown herein is of the type disclosed in U.S. Pat. No. 5,232,020, incorporated herein by reference, having two snap-action locking couplings 72a, 72b with lock release buttons. As described in U.S. Pat. No. 5,232,020, but not shown herein, each coupling comprises an internal male connector on the reservoir side and an internal female connector on the pad side of the coupling, or vice versa. The internal male connectors are housed together in a unitary molded mount, and the internal female connectors are similarly housed together in a unitary molded mount to facilitate simultaneous connection of the couplings. External male connectors are press fitted into the sheath 16 and associated inlet and outlet lines 18, 20. The couplings 72a, 72b are further provided with internal shut off valves which automatically close fluid lines 18, 20 when the couplings 72a, 72b are disconnected. When the releasable joint 40 is fully engaged, the pad 12, inlet line 18, outlet line 20, pump 22, and joint 40 in combination define a continuous, closed, circulatory system flowpath commencing and terminating at the fluid reservoir 14.

In an alternate embodiment not shown, the releasable joint 40 can be excluded from the fluid lines 18, 20 of the therapeutic treatment device 10, so that the pad 12 remains fixedly connected to the fluid lines 18, 20 for the life of the device. In all other respects the resulting jointless therapeutic treatment device is substantially identical to the jointed therapeutic treatment device of FIG. 1. Omission of the releasable joint 40 from the therapeutic treatment device does not defeat the closed circulatory character of the system flowpath, nor substantially modify the remaining structure or functional operation of the jointless therapeutic treatment device as compared to the therapeutic treatment device 10 having a releasable joint 40.

The therapeutic treatment device 10 of FIG. 1 further comprises a flow restriction positioned in the system flowpath downstream of the pad flowpath 54 (obscured from view in FIG. 1 by the sheath 16). The flow restriction is positioned in the pad outlet port 66 or the outlet line 20 to provide a fluid backpressure in the pad flowpath 54. The fluid backpressure impedes the flow of treatment fluid back to the reservoir 14 via the pad outlet port 66 and outlet line 20, thereby desirably inflating the pad 12 with pressurized treatment fluid. The flow restriction can be substantially any element that diminishes the cross-sectional area of the downstream system flowpath. The flow restriction can have a fixed reduced cross-section, such as an in-line orifice, a crimp, or reduced-size tubing, or can have a variable reduced cross-section, such as a check valve or a selectively adjustable valve. A preferred flow restriction is a conventional pressure relief valve positioned in the outlet line 20 proximal to the pad outlet port 66. The valve remains closed until a preset relief pressure is exceeded in the pad flowpath 54. The relief pressure can be preset to any pressure above the ambient atmospheric pressure, but is typically preset at about 1 psi greater than the ambient atmospheric pressure.

Each of the above-recited embodiments of the therapeutic treatment device is operated in substantially the same manner as described hereafter. Operation is initiated by filling the fluid reservoir 14 with a fresh nonambient temperature treatment fluid and securing the lid 30 to passively maintain the nonambient temperature of the treatment fluid therein. The pad 12 is positioned on the desired treatment region of the body and the inlet and outlet lines 18, 20 and intervening pad flowpath 54 are placed in fluid communication with the fluid reservoir 14.

The pad flowpath 54 is charged with fresh treatment fluid by first charging the interior chamber of the bulb pump 22. Charging of the bulb pump 22 is effectuated by sequentially compressing the bulb pump 22 and then allowing it to elastically expand back to its original memorized shape. Expansion of the bulb pump 22 draws fresh nonambient temperature treatment fluid through the inlet line 18 across a conventional check valve (not shown), such as a ball valve, positioned at the pump inlet port 24. The pump inlet valve permits fluid flow from the reservoir 14 in the direction of the pump 22, but prevents fluid flow from the pump 22 in the direction of the reservoir 14. As fresh treatment fluid enters the bulb pump 22 across the pump inlet valve, another conventional check valve, shown herein as a ball valve 74 positioned at the pump outlet port 26, permits fluid flow through the inlet line 18 in the direction of the pad 12, but prevents fluid flow from the pad 12 in the direction of the pump 22. A transparent window 76 is provided in the sheath 16 that is formed from a clear rigid plastic or glass enabling the user to view operation of the pump outlet valve 74 and the flow of the treatment fluid therethrough. A bulb pump and check valves having utility herein are described in U.S. patent application No. 08/199,333, incorporated herein by reference.

When the interior chamber of the bulb pump 22 is substantially filled with fresh treatment fluid, the treatment fluid is transferred to the pad flowpath 54 by manually compressing the bulb pump 22, thereby driving the fresh treatment fluid across the pump outlet valve through the inlet line 18 into the pad flowpath 54. The force of the treatment fluid as the bulb pump 22 is compressed also closes the pump inlet valve preventing any fresh fluid from returning to the reservoir 14 via the pump inlet port 24. This procedure is repeated as often as necessary until the pad flowpath 54 is completely filled with fresh treatment fluid at a pressure up to the preset pressure of the pressure relief valve.

As treatment of the affected body region proceeds over time, the treatment fluid residing in the pad flowpath 54 thermally equilibrates toward the ambient temperature of the external environment, diminishing the effectiveness of the treatment. The treatment fluid in the pad flowpath 54 is deemed spent when it thermally equilibrates to a predetermined temperature approaching the ambient temperature, at which time the spent treatment fluid is desirably replaced with fresh nonambient temperature treatment fluid from the reservoir 14.

The spent treatment fluid is replaced by substantially repeating the above-described procedure. Because the pad flowpath 54 is filled with spent treatment fluid, however, the fresh treatment fluid must be transferred from the bulb pump 22 into the pad flowpath 54 with a sufficient displacement force to open the pressure relief valve in the outlet line 20 and drive the spent treatment fluid from the pad flowpath 54 back to the reservoir 14 via the outlet line 20. In the reservoir 14, the spent treatment fluid is diluted by the greater volume of fresh treatment fluid, thereby restoring the spent treatment fluid to an effective nonambient treatment temperature for future circulation back into the pad flowpath 54. This treatment fluid circulation cycle can be repeated at periodic time intervals thereafter as often as desired for effective treatment of the body.

Figure 5:
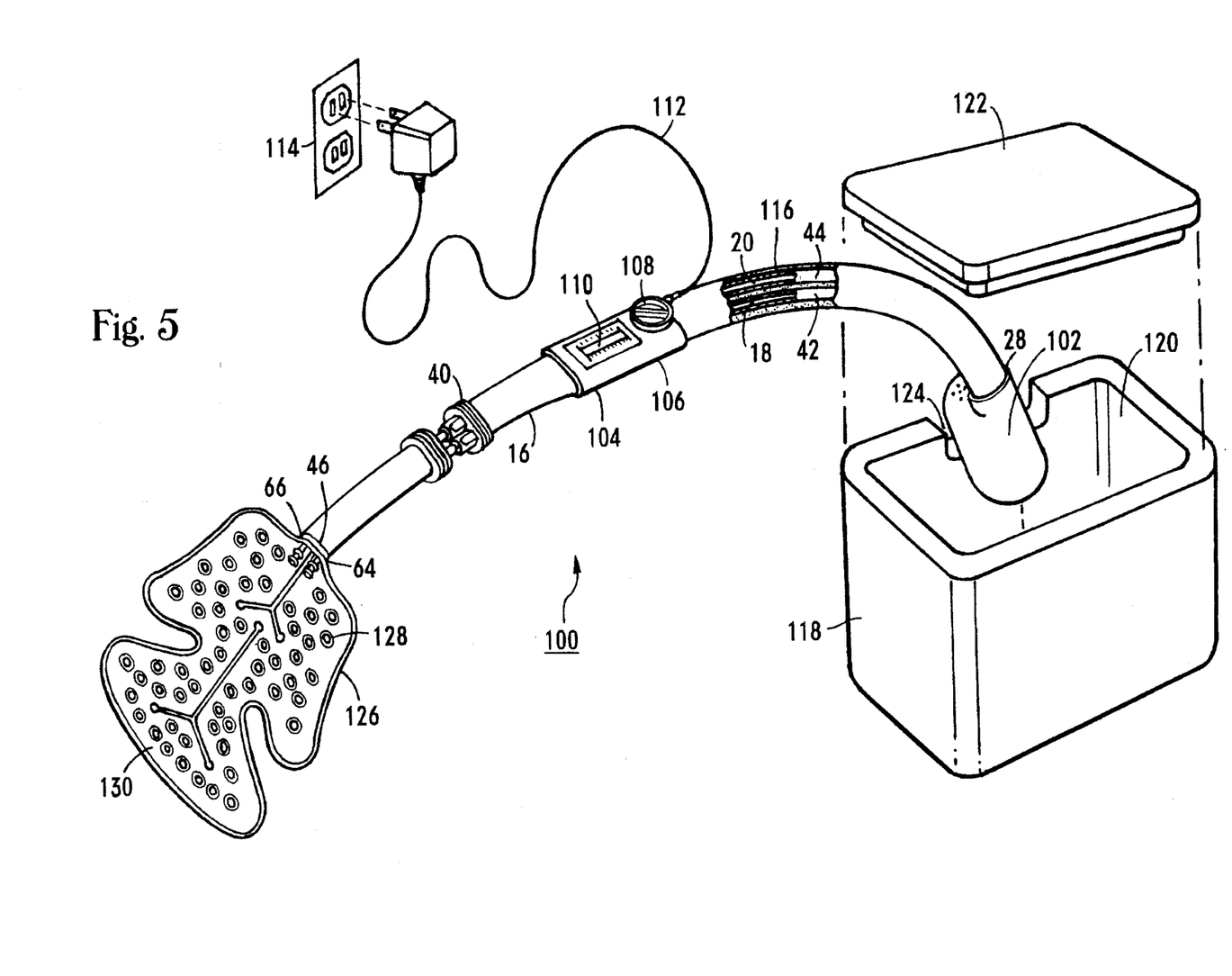
FIG. 5 is a perspective view of an alternate embodiment of a therapeutic treatment device of the present invention having a fluid inlet line, a fluid outlet line, and a motor-driven submersible pump positioned across the fluid inlet line.

Referring to FIG. 5, another embodiment of a therapeutic treatment device is shown and generally designated 100. Identical reference characters are used to identify elements common to both the therapeutic treatment device 100 and the therapeutic treatment device 10. The device 100, however, replaces the in-line, manual bulb pump 22 of the device 10 with an in-line, electrically-powered, motor-driven submersible pump 102 positioned at the reservoir end 28 of the inlet and outlet lines 18, 20. The submersible pump 102 is preferably a conventional, single-speed impeller pump having a substantially constant output.

The therapeutic treatment device 100 also provides a control unit 104 proximal to the position occupied by the bulb pump 22 in the device 10. The control unit 104 is integral with the sheath 16 and has a rigid housing 106 with a manually adjustable valve control knob 108, a temperature display 110, and an electrical connector 112 mounted thereon. The control knob 108 engages a conventional adjustable flow restrictor valve (not shown) positioned in the outlet line 20 at the location of the control unit 104 for manual adjustment of the valve in a manner described hereafter. The temperature display 110, in association with a temperature measuring means positioned in the outlet line 20, provides a visual readout of the fluid temperature therein. The temperature display 110 and measuring means are preferably integrally embodied within a conventional liquid thermometer.

The electrical connector 112 is a disconnectable power cord and transformer assembly enabling electrical communication between the submersible pump 102 and an external power source, such as a conventional ac wall plug 114. Electrical power is conducted from the electrical connector 112 to the pump 102 via an internal power line 116 extending through the sheath 16 in parallel with the inlet and outlet lines 18, 20. Alternatively, the device 100 can be provided with an internal power pack (not shown) in the control unit 104 which conducts electrical power to the pump 102 via the internal power line 116, thereby eliminating the electrical connector 112 from the device 100.

The fluid reservoir 118 of the therapeutic treatment device 100 is similar to the fluid reservoir 14 of the device 10 except that the present reservoir 118 is modified with a substantially larger opening 120 to receive the submersible pump 102 and the reservoir end 28 of the sheath 16. Accordingly, the fluid reservoir 118 is a wide-mouth heat-insulative container, such as a conventional insulated picnic cooler. The fluid reservoir 118 has a cover 122 positioned over the opening 120 for passively maintaining the nonambient temperature of the treatment fluid therein and has a slot 124 formed at the opening 120 that permits the sheath 16 to extend into the reservoir 118 when covered.

The pad 126 of the therapeutic treatment device 100 is configured nearly identically to the pad 12 of the device 10 except that the circular welds 128 of the pad 126 are spaced closer together to decrease the height and correspondingly the volume of the pad flowpath 130. Because the treatment fluid of the device 100 is continuously circulated through the pad flowpath 130, the treatment fluid in the pad flowpath 130 does not readily equilibrate to the ambient temperature of the external environment and, therefore, less treatment fluid is required to maintain the desired nonambient temperature at the body surface. The therapeutic treatment device 100 is substantially the same as the therapeutic treatment device 10 in all other respects, having a sheath 16, an inlet line 18, an outlet line 20, and a releasable joint 40, all of similar construction.

Operation of the therapeutic treatment device 100 is substantially as described in U.S. Pat. No. 5,241,951, incorporated herein by reference. In the low temperature embodiment, the fluid reservoir 118 is initially filled with a fresh low-temperature therapeutic treatment fluid such as ice water. The submersible pump 102 is submersed in the treatment fluid with the sheath 16 extending from the reservoir 118, thereby maintaining the inlet and outlet lines 18, 20 and intervening pad flowpath 130 in fluid communication with the treatment fluid in the reservoir 118. The cover 122 is secured to the reservoir 118 and the pad 126 is positioned on the desired treatment region of the body. The pump 102 is electrically activated to continuously circulate the treatment fluid through the pad flowpath 130 by cycling the fluid from the fluid reservoir 118 via the inlet line 18, through the pad flowpath 130, and back to the fluid reservoir 118 via the outlet line 20. The fluid circulation cycle is performed continuously at a substantially constant pump output for the duration of the desired treatment period.

Temperature control of the pad 126 during the circulation cycle is achieved by regulating the flow rate of treatment fluid through the pad flowpath 130. In accordance with the present embodiment, the user regulates the flow rate of the treatment fluid by moving the control knob 108 to correspondingly adjust the cross-sectional area of the flowpath across the flow restrictor valve positioned in the outlet line 20 while the pump 102 operates continuously at a constant output indicated by the speed and pumping pressure of the pump. If the control knob 108 is moved to reduce the cross-sectional area of the flow restrictor valve, the temperature of the pad 126 is increased. Conversely, if the control knob 108 is moved to increase the cross-sectional area of the flow restrictor valve, the temperature of the pad 126 is decreased. Temperature control is facilitated by monitoring the temperature of the treatment fluid in the outlet line 20 using the temperature display 110 on the control unit 104. It is further noted that the adjustable flow restrictor valve acts to regulate the backpressure in the pad flowpath 130 as a function of the cross-sectional area of the valve flowpath.

The high temperature embodiment of the device 100 is primarily distinguishable from the low temperature embodiment described above in that a heated fluid is substituted for ice water. The heated fluid is preferably water which is heated to a temperature exceeding the ambient temperature of the surrounding environment. The temperature of the pad 126 is decreased by partially closing the adjustable flow restrictor valve in the outlet line 20 to diminish flow rate of heated fluid therethrough, while the temperature of the pad 126 is increased by opening the adjustable flow restrictor valve to increase the flow rate of heated fluid therethrough.

It is apparent that other equivalent means of regulating the flow rate of treatment fluid through the pad flowpath to control the temperature of the pad not shown herein are available within the scope of the present invention. For example, a therapeutic treatment device can be provided within the scope of the present invention that is substantially the same as the device 10, wherein the flow rate of nonambient temperature treatment fluid through the pad flowpath is regulated by replacing the fixed-output pump with a variable-output pump having an adjustable output control mechanism and eliminating the adjustable flow restrictor valve in the outlet line. Thus, the flow rate of the fluid through the pad flowpath is regulated to control the temperature of the pad in an equivalent manner by moving a power control knob on the pump to correspondingly adjust the pump. Thus, if it is desired to lower the temperature of the pad in the low temperature embodiment of the device, the pump output is increased. Conversely, if it is desired to raise the temperature of the pad in the low temperature embodiment of the device, the pump output is decreased. Rather than placing the adjustable flow restrictor valve in the outlet line of the present variable-output pump embodiment, alternate means can be placed in the outlet line to obtain a desired backpressure in the pad flowpath, such as an in-line orifice, a crimp, reduced-size tubing, or a check valve.

Figure 6A:
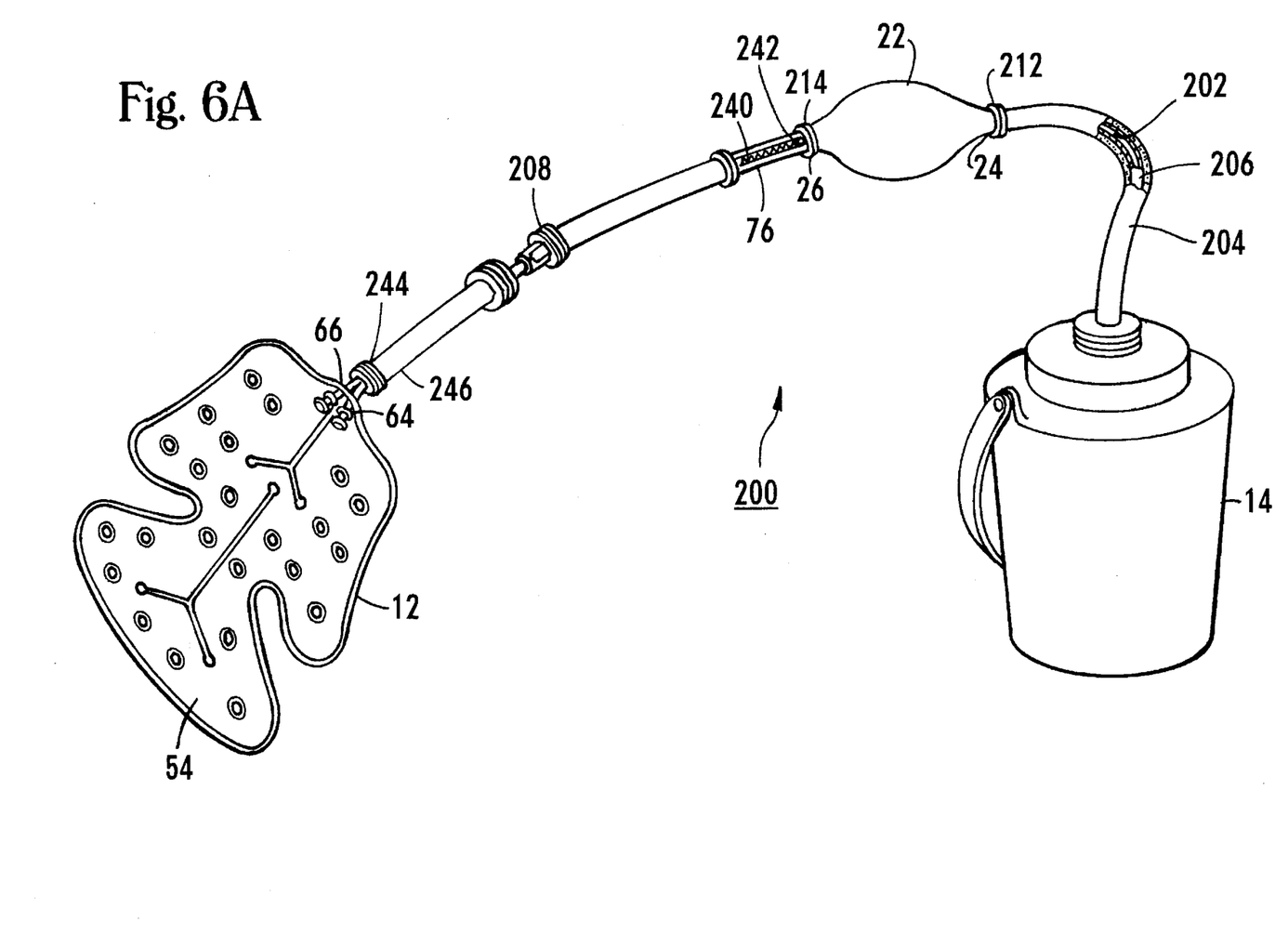
FIG. 6A is a perspective view of another alternate embodiment of a therapeutic treatment device of the present invention having a single fluid flow line and a manual bulb pump positioned across the flow line.

Referring to FIG. 6A, a further embodiment of a therapeutic treatment device is shown and generally designated 200. Identical reference characters are used to identify elements common to both the therapeutic treatment device 200 and the therapeutic treatment device 10. The device 200 is substantially the same as the device 10, but the device 200 has only one fluid flow line 202 providing a single fluid pathway between the pad 12 and the fluid reservoir 14 to alternately supply fresh nonambient temperature fluid to the pad flowpath 54 from the fluid reservoir 14 via the pad inlet port 64 and return spent treatment fluid to the fluid reservoir 14 from the pad flowpath 54 via the pad outlet port 66. The flow line 202 is a single longitudinal bore extending through a heat-insulative sheath 204 having a liner tube 206 retained therein in substantially the same manner as described above with respect to the device 10 and the sheath 16. The sheath 204 also has a releasable joint 208 positioned proximal to the pad 12 in a manner similar to the device 10 and the joint 40.

The present therapeutic treatment device 200 has a pump assembly positioned in the flow line 202 between the pad 12 and the fluid reservoir 14. The pump assembly includes a bulb pump 22 having an inlet port 24 and an outlet port 26, and further includes an inlet leak-back valve positioned at the pump inlet port 24 and an outlet leak-back valve positioned at the pump outlet port 26. The leak-back valves selectively permit substantially unrestricted flow of treatment fluid at a full flow rate in the direction of the pad flowpath 54, while continuously permitting restricted flow of treatment fluid in the direction of the fluid reservoir 14 at a substantially reduced flow rate. The pump assembly is described in greater detail hereafter with reference to FIGS. 7A and 7B.

Figure 7A:
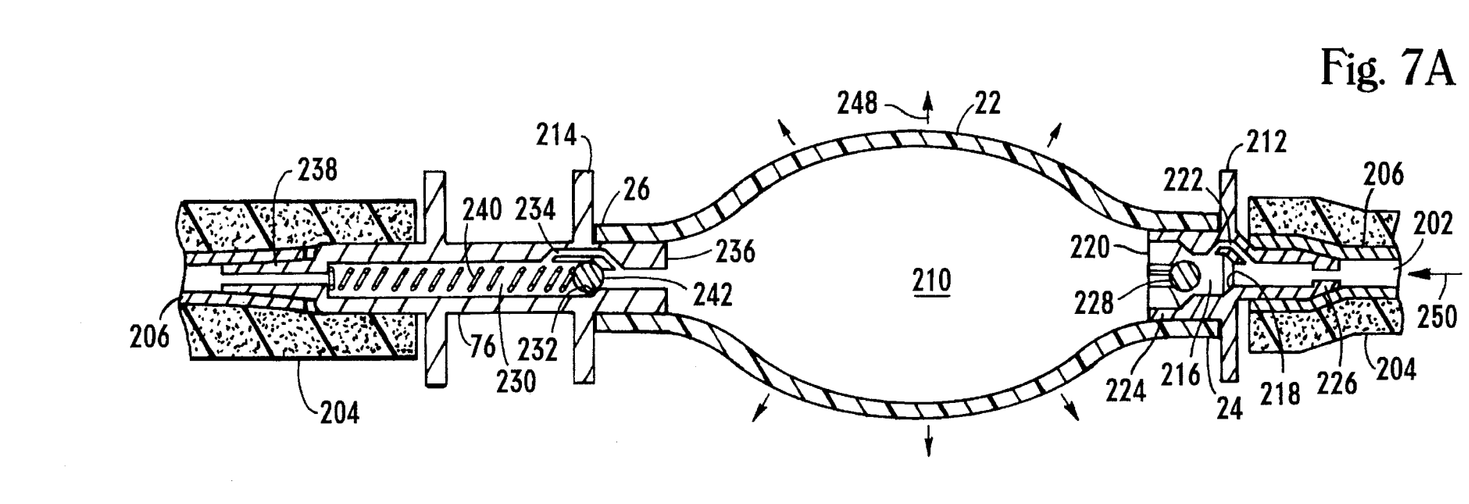
FIG. 7A is a cross-sectional elevational view of the manual bulb pump of FIG. 6 in the intake mode.
Figure 7B:
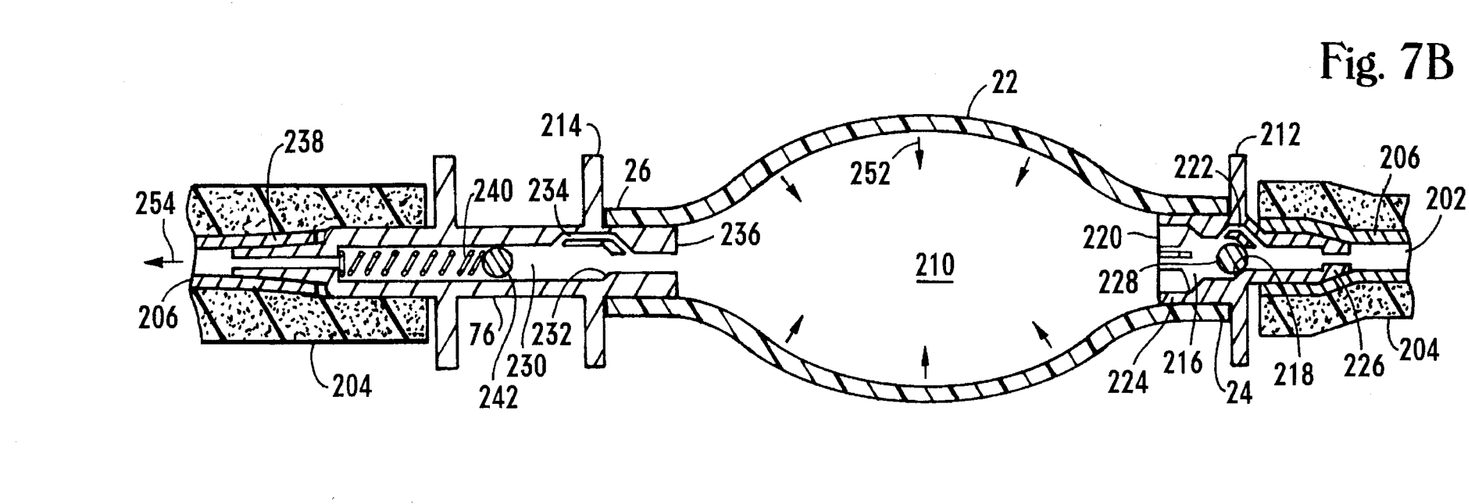
FIG. 7B is a cross-sectional elevational view of the manual bulb pump of FIG. 6A in the discharge mode.

The pump assembly comprises the bulb pump 22 having a hollow interior fluid chamber 210 in fluid communication with the exterior of the bulb pump 22 via the pump inlet and outlet ports 24, 26. The pump assembly further comprises the inlet leak-back valve integrally contained within an inlet valve housing 212 and the outlet leak-back valve integrally contained within an outlet valve housing 214. The inlet and outlet valve housings 212, 214 are formed from a rigid material, such as a rigid plastic. The inlet valve housing 212 has an inlet valve chamber 216, an inlet valve seat 218, ball retention vanes 220, an inlet leak-back channel 222, an inlet internal male end 224, and an inlet external male end 226. Displacably retained within the inlet valve chamber 216, is a ball 228 functioning as a valve plunger. The inlet leak-back channel 222 is a very narrow passageway relative to the inlet valve chamber 216 providing limited fluid communication across the inlet leak-back valve when the valve is in the closed position with the ball 228 against the inlet valve seat 218 as described hereafter. Fluid-tight connection of the bulb pump 22 to the flow line 202 is provided in part by receiving the inlet internal male end 224 of the inlet valve housing 212 within the pump inlet port 24 and receiving the inlet external male end 226 within the liner tube 206.

The outlet valve housing 214 has an outlet valve chamber 230, an outlet valve seat 232, an outlet leak-back channel 234, an outlet internal male end 236, and an outlet external male end 238. A spring 240 and a flow indicator ball 242 are displacably retained within the outlet valve chamber 230 and the transparent flow window 76 is integral with the outlet valve housing 214 enabling the user to observe operation of the spring 240 and ball 242 retained therein. The outlet leak-back channel 234 is a very narrow passageway relative to the outlet valve chamber 230 providing limited fluid communication across the outlet leak-back valve when the valve is in the closed position with the ball 242 against the outlet valve seat 232 as described hereafter. It is noted that the inlet and outlet valves of the device 10 can be configured substantially identically to the inlet and outlet leak-back valves of the device 200 absent the leak-back channels 222, 234.

Fluid-tight connection of the bulb pump 22 to the flow line 202 is further provided by receiving the outlet internal male end 236 of the outlet valve housing 214 within the pump outlet port 26 and receiving the outlet external male end 238 within the liner tube 206. The flow indicator ball 242 functions both as a displacable valve plunger and as a flow indicator for the treatment fluid. The ball 242 preferably has a distinctively visible color, such as red, to enhance its visibility to the user when viewed through the transparent flow window 76.

The inlet and outlet leak-back valves have been described above as having inlet and outlet leak-back channels 222, 234, respectively, enabling limited fluid communication across the leak-back valves when the valves are in the closed position. It is understood, however, that this function can be equivalently performed in the absence of the leak-back channels 222, 234 by providing small notches in the valve seats 218, 232 that permit limited fluid flow past the valve seats 218, 232 when the respective balls 228, 242 are seated therein.

Figure 6B:
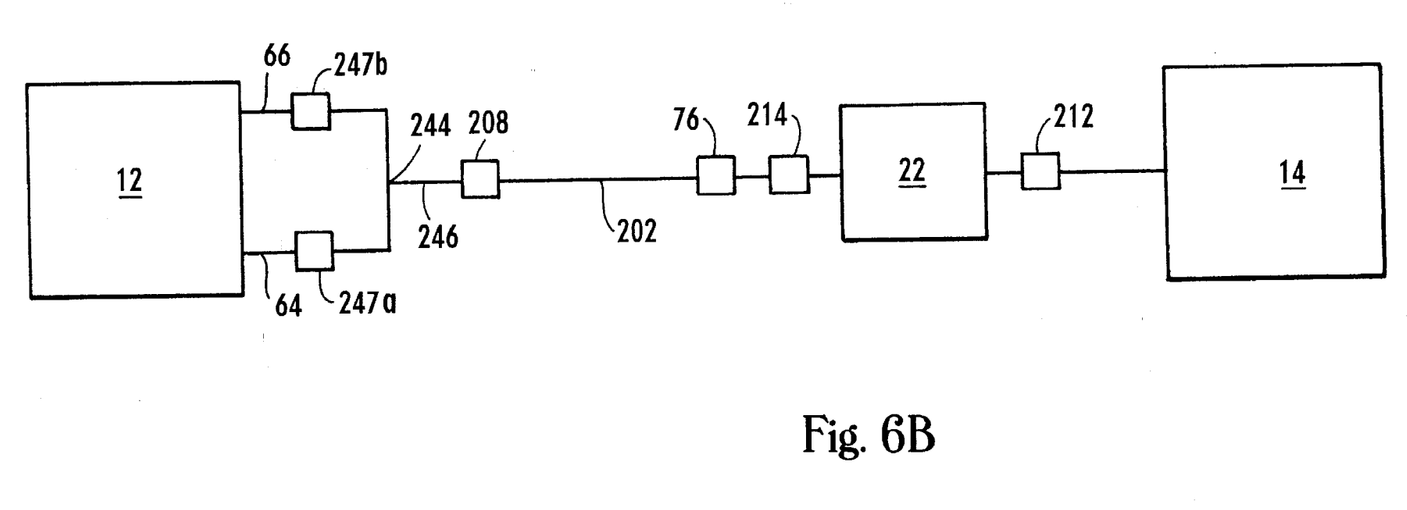
FIG. 6B is a schematic representation of the therapeutic treatment device shown in FIG. 6A.

A plurality of additional in-line fittings and valves enable selective supply or return of the nonambient treatment fluid between the pad flowpath 54 and the fluid reservoir 14 via the flow line 202 in cooperation with the inlet and outlet leak-back valves. In particular, a three-branched "Y" fitting 244 joins the pad inlet and outlet ports 64, 66 with the flow line 202 at the pad end 246 of the line 202. A conventional one-way check valve (shown as 247a in FIG. 6B) is positioned in or near one branch of the "Y" fitting 244 at the pad inlet port 64 to selectively permit flow across the port 64 only in the direction of the pad flowpath 54 and not in the direction of the reservoir 14. A flow restriction (shown as 247b in FIG. 6B) is positioned in or near another branch of the "Y" fitting 244 at the pad outlet port 66 to permit flow across the port 66 in the direction of the reservoir 14 while preventing, or at least impeding, flow across the port 66 in the direction of the pad flowpath 54. The flow restriction 247b at the pad outlet port 66 can have a variable reduced cross-section, such as a conventional check valve or a selectively adjustable valve, or the flow restriction 247b can have a fixed reduced cross-section, such as an in-line orifice, a crimp, or reduced-size tubing. FIG. 6B schematically shows the relationship between the primary structural elements of the therapeutic treatment device 200.

With reference to FIGS. 6A and 6B, therapeutic treatment device 200 is operated by filling the fluid reservoir 14 with a fresh nonambient temperature treatment fluid and positioning the pad 12 on the desired treatment region of the body in substantially the same manner as described above with respect to the therapeutic treatment device 10. The pad flowpath 54, which is initially in a substantially evacuated condition, is charged with the fresh treatment fluid by first manually compressing the bulb pump 22 to evacuate the interior chamber 210. Thereafter, the bulb pump 22 is allowed to elastically expand in the direction of the arrows 248, as shown in accordance with the intake mode of FIG. 7A. As the bulb pump 22 expands, the fresh treatment fluid is drawn through the flow line 202 in the direction of the arrow 250, and urges the ball 228 against the retention vanes 220. As a result, the fresh treatment fluid is permitted to enter the interior chamber 210 via the pump inlet port 24. At the same time, the flow indicator ball 242 is biased against the outlet valve seat 232 by the force of the spring 240, substantially impeding significant amounts of fluid from entering the interior chamber 210 via the pump outlet port 26.

When the bulb pump 22 is fully expanded with the fresh treatment fluid, it is manually compressed in the direction of the arrows 252, as shown in accordance with the discharge mode of FIG. 7B. The degree of compression force that the user applies to the bulb pump 22 is regulated by the user in correspondence with the position of the flow indicator ball 42 and spring 240, as observed through the transparent flow display section 76. For an optimal flow rate and fluid pressure in the flow line 202, the bulb pump 22 is compressed with a force that maintains the flow indicator ball 242 at a position about midway within the flow display section 76 as shown in FIG. 7B.

As the bulb pump 22 compresses, the fresh treatment fluid is driven from the interior chamber 210 toward the pump outlet port 26. The force of the fresh treatment fluid displaces the flow indicator ball 242 away from the outlet valve seat 232 by compressing the spring 240 and permits the fresh treatment fluid to exit the interior chamber 210 via the pump outlet port 26 in the direction designated by the arrow 254. The fresh treatment fluid travels the remaining length of the flow line 202 and the bulk, if not all, of the fresh treatment fluid is diverted by the flow restriction 247b at the pad outlet port 66 into the pad inlet port 64. The fluid pressure urges the check valve 247a at the pad inlet port 64 open permitting the fresh treatment fluid to enter the pad flowpath 54. The force of the treatment fluid as the bulb pump 22 is compressed also urges the ball 228 against the inlet valve seat 218 substantially impeding significant amounts of fresh fluid from returning to the reservoir 14 via the pump inlet port 24. This procedure is repeated as often as necessary until the pad flowpath 54 is substantially filled with fresh treatment fluid.

While treatment of the affected body region proceeds over time, the spent treatment fluid residing in the pad flowpath 54 slowly leaks back to the fluid reservoir 14 through the open flow restriction 247b at the pad outlet port 66 and the flow line 202. Fluid flow is enabled across the bulb pump 22 via the open inlet and outlet leak-back channels 222, 234. When the spent treatment fluid returns to the reservoir 14, it is diluted therein by the greater volume of fresh treatment fluid, restoring the spent treatment fluid to an effective nonambient treatment temperature for future circulation back into the pad flowpath 54. After the pad flowpath 54 loses a sufficient quantity of spent treatment fluid, the pad 12 thermally equilibrates toward the ambient temperature of its surroundings. Accordingly, the above-described procedure of fluid intake and fluid discharge with respect to the bulb pump 22 is repeated to refill the pad flowpath 54 with fresh treatment fluid.

In an alternate embodiment of the above-recited therapeutic treatment device 200 not shown but described hereafter, a reversible pump is substituted for the compressible bulb pump 22 in the fluid flow line 202. The reversible pump is a manual or motor-driven pump, such as a rotary impeller pump, for selectively driving fluid through the fluid flow line 202 in the direction of the pad flowpath 54 or the fluid reservoir 14. The alternate embodiment has a pair of one-way valves positioned at the pad inlet and outlet ports 64, 66 respectively, but obviates the leak-back valves at the pump inlet and outlet ports 24, 26.

Figure 8:
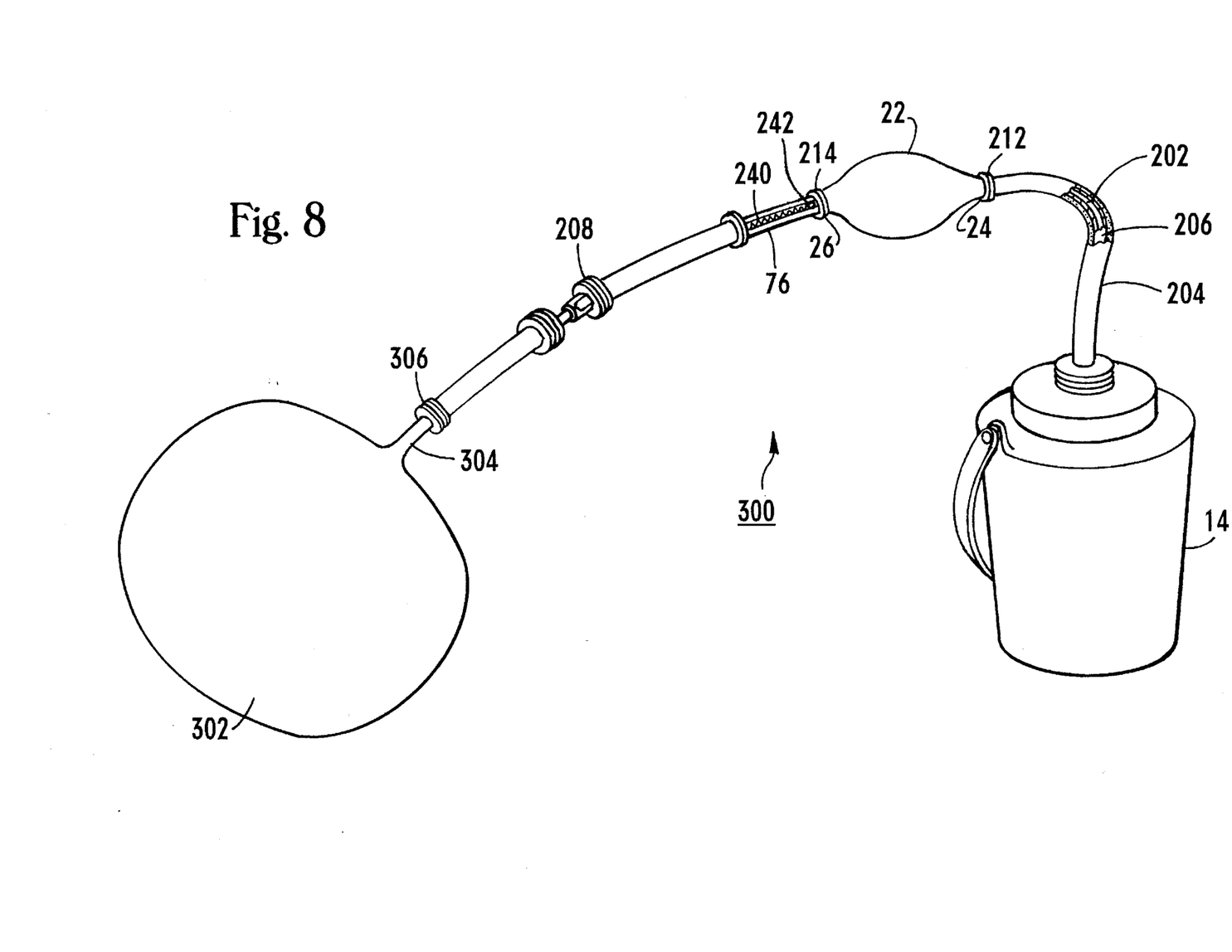
FIG. 8 is a perspective view of yet another alternate embodiment of a therapeutic treatment device of the present invention having a single fluid flow line and a manual bulb pump positioned across the flow line.

Referring to FIG. 8, another embodiment of a therapeutic treatment device is shown and generally designated 300. Identical reference characters are used to identify elements common to the therapeutic treatment device 300 and the therapeutic treatment device 200. The device 300 is substantially the same as the device 200, but a relatively larger volume bladder 302 having a single port 304 in fluid communication with the fluid flow line 202 is substituted for the pad 12 of the device 200 having separate inlet and outlet ports 64, 66.

The bladder 302 has a three-dimensional configuration with a pliant heat transfer surface that is conformable to the contours of the external skin surface of the user. The bladder 302 is distinguishable from a planar pad insofar as the bladder 302 has a significant thickness relative to the length and width of the bladder 302. A straight coupling 306 joins the fluid flow line 202 with the port 304. The coupling 306 is substantially free of any flow restrictions or valves. Although a compressible bulb pump 22 having leak-back valves at the pump inlet and outlet ports 24, 26 is shown positioned in the fluid flow line 202, it is within the scope of the present invention to substitute substantially any other manual or motor-driven pump enabling fluid leak-back across the pump for the bulb pump 22.

The therapeutic treatment device 300 is operated by charging a relatively large volume of fresh treatment fluid to the bladder 302 from the fluid reservoir 14 by means of the pump 22 via the fluid flow line 202 and the port 304. As the fresh treatment fluid is being pumped, the pumping pressure pressurizes the treatment fluid in the bladder 302 to a fluid pressure exceeding the ambient pressure. Once pumping ceases, however, no further pumping pressure is exerted on the treatment fluid in the bladder 302. The elevated fluid pressure in the bladder 302 consequently drives spent treatment fluid back to the fluid reservoir 14 across the leak-back valves at a restricted flow rate.

The restricted flow rate is sufficiently slow that the volume of treatment fluid in the bladder 302 at any given time is adequate to provide therapeutic treatment to the body for an extended period of time. When the volume of treatment fluid in the bladder 302 drops below a predetermined level, however, pumping is resumed to charge fresh treatment fluid to the bladder 302. The fresh treatment fluid pumped into the bladder 302 mixes with the residual treatment fluid remaining in the bladder 302 and the mixture equilibrates to an acceptable nonambient temperature enabling continued therapeutic treatment of the body.

While the forgoing preferred embodiments of the invention have been described and shown, it is understood that alternatives and modifications, such as those suggested and others, may be made thereto and fall within the scope of the invention.

We claim:

1. A therapeutic treatment device for heating or cooling a treatment region of the body with a nonambient temperature treatment fluid comprising:

a heat transfer element having an element port;

a passive fluid reservoir for retaining a nonambient temperature treatment fluid;

a fluid flow line having two ends, a first end in fluid communication with said fluid reservoir and a second end in fluid communication with said element port; and a pump in fluid communication with said fluid flow line for driving treatment fluid from said fluid reservoir to said heat transfer element via said fluid flow line at a pumping flow rate when said pump is activated; and means in fluid communication with said heat transfer element for leaking back treatment fluid from said heat transfer element to said fluid reservoir when said pump is inactivated at a leak-back flow rate substantially less than said pumping flow rate.

2. A therapeutic treatment device as recited in claim wherein said pump is a manually compressible elastic bulb positioned in said fluid flow line having a pump inlet port and a pump outlet port.

3. A therapeutic treatment device as recited in claim wherein said leak-back means comprises a leak-back valve positioned at said pump outlet port permitting flow of treatment fluid at said pumping flow rate in the direction of said heat transfer element and permitting flow of treatment fluid in the direction of said fluid reservoir at said leak-back flow rate.

4. A therapeutic treatment device as recited in claim 3 wherein said leak-back means comprises a leak-back valve positioned at said pump inlet port permitting flow of treatment fluid at said pumping flow rate in the direction of said heat transfer element and permitting flow of treatment fluid in the direction of said fluid reservoir at said leak-back flow rate.

5. A therapeutic treatment device as recited in claim 1 wherein said heat transfer element is pliant and said element port is an element inlet port, and further wherein said heat transfer element has an element outlet port.

6. A therapeutic treatment device as recited in claim 5 wherein said pump is a manually compressible elastic bulb positioned in said fluid flow line having a pump inlet port and a pump outlet port.

7. A therapeutic treatment device as recited in claim 6 further comprising a three-branched fitting connecting said fluid flow line to said element inlet port and said element outlet port.

8. A therapeutic treatment device as recited in claim 6 further comprising a one-way valve positioned at said element inlet port selectively permitting flow of treatment fluid at said pumping flow rate in the direction of said heat transfer element, while substantially preventing flow of treatment fluid in the direction of said fluid reservoir.

9. A therapeutic treatment device as recited in claim 6 wherein said leak-back means comprises a leak-back valve positioned at said pump outlet port permitting flow of treatment fluid at said pumping flow rate in the direction of said heat transfer element and permitting flow of treatment fluid in the direction of said fluid reservoir at said leak-back flow rate.

10. A therapeutic treatment device as recited in claim 6 further comprising a flow restriction positioned at said element outlet port reducing the cross-sectional area of said element outlet port and permitting flow of treatment fluid in the direction of said fluid reservoir at a flow rate substantially less than said pumping flow rate.

11. A therapeutic treatment device as recited in claim 10 wherein said flow restriction is a one-way valve substantially preventing flow of treatment fluid in the direction of said heat transfer element.

12. A therapeutic treatment device as recited in claim 6 wherein said leak-back means comprises a leak-back valve positioned at said pump inlet port permitting flow of treatment fluid at said pumping flow rate in the direction of said heat transfer element and permitting flow of treatment fluid in the direction of said fluid reservoir at said leak-back flow rate.

* * * * *

UNITED STATES PATENT AND TRADEMARK OFFICE
CERTIFICATE OF CORRECTION

PATENT NO. : 5,507,792
DATED : April 16, 1996
INVENTOR(S) : Bradley R. Mason et al It is certified that error appears in the above-indentified patent and that said Letters Patent is hereby corrected as shown below:

Column 14, line 66: delete "42" and insert --242--.

Column 16, line 57: after "claim", insert --1--.

Column 16, line 61, after "claim ", insert --2--.

Signed and Sealed this

Twentieth Day of August, 1996

Attest:

BRUCE LEHMAN

Attesting Officer    Commissioner of Patents and Trademarks